United States Patent
Cowan et al.

(10) Patent No.: US 11,260,237 B1
(45) Date of Patent: Mar. 1, 2022

(54) WEARABLE DEFIBRILLATOR WITH OUTPUT STAGE HAVING DIVERTING RESISTANCE

(71) Applicant: West Affum Holdings Corp., Grand Cayman (KY)

(72) Inventors: Kenneth Frederick Cowan, Kirkland, WA (US); Joseph Sullivan, Kirkland, WA (US); Brian J. Bennett, Redmond, WA (US)

(73) Assignee: West Affum Holdings Corp., Grand Cayman (KY)

( * ) Notice: Subject to any disclaimer, the term of this patent is extended or adjusted under 35 U.S.C. 154(b) by 79 days.

(21) Appl. No.: 16/181,604

(22) Filed: Nov. 6, 2018

Related U.S. Application Data

(60) Provisional application No. 62/583,924, filed on Nov. 9, 2017.

(51) Int. Cl.
 *A61N 1/39* (2006.01)
 *A61N 1/04* (2006.01)

(52) U.S. Cl.
 CPC ........... *A61N 1/3904* (2017.08); *A61N 1/046* (2013.01); *A61N 1/0484* (2013.01); *A61N 1/3925* (2013.01); *A61N 1/3993* (2013.01)

(58) Field of Classification Search
 CPC .... A61N 1/3904; A61N 1/046; A61N 1/0484; A61N 1/3925; A61N 1/3993
 (Continued)

(56) References Cited

U.S. PATENT DOCUMENTS

| 3,724,355 A | 4/1973 | Unger |
| 3,724,455 A | 4/1973 | Unger |

(Continued)

FOREIGN PATENT DOCUMENTS

WO 1998039061 A2 9/1998

OTHER PUBLICATIONS

Klein, H. U., Goldenberg I., & Moss, A. J., Risk Stratification for Implantable Cardioverter Defibrillator Therapy: The Role of the Wearable Cardioverter-Defibrillator, Clinical update, European Heart Journal, May 31, 2013, pp. 1-14, doi:10.1093/eurheartj/eht167, European Society of Cardiology.

(Continued)

*Primary Examiner* — Mallika D Fairchild
*Assistant Examiner* — Naveed R. Kolia
(74) *Attorney, Agent, or Firm* — Spectrum IP Law Group LLC

(57) ABSTRACT

In embodiments, an external defibrillator has an electrical circuit with a special output stage for the high-voltage defibrillation pulse. The output stage includes switches that can turn on for delivering the pulse, and off during all other times. The output stage also includes a diverting resistance to divert electrical current that could leak into the patient while a capacitor is being charged. An optional detector may notify if a component is malfunctioning. An advantage can be that an external defibrillator may be created according to embodiments that uses, in its output stage, semiconductor switches instead of relays. As semiconductor switches weigh less and occupy less volume than relays, an external defibrillator according to embodiments may have less weight and volume. Especially in wearable defibrillator applications, less weight means less effort to carry and less volume means easier concealment under clothing.

28 Claims, 10 Drawing Sheets

(58) Field of Classification Search
USPC .......................................................... 607/5
See application file for complete search history.

(56) References Cited

U.S. PATENT DOCUMENTS

| | | |
|---|---|---|
| 4,583,524 A | 4/1986 | Hutchins |
| 4,619,265 A | 10/1986 | Morgan et al. |
| 4,928,690 A | 5/1990 | Heilman et al. |
| 4,955,381 A | 9/1990 | Way et al. |
| 5,078,134 A | 1/1992 | Heilman et al. |
| 5,228,449 A | 7/1993 | Christ et al. |
| 5,348,008 A | 9/1994 | Bornn et al. |
| 5,353,793 A | 10/1994 | Bornn |
| RE34,800 E | 11/1994 | Hutchins |
| 5,394,892 A | 3/1995 | Kenny |
| 5,405,362 A | 4/1995 | Kramer et al. |
| 5,474,574 A | 12/1995 | Payne et al. |
| 5,662,690 A | 9/1997 | Cole et al. |
| 5,782,878 A | 7/1998 | Morgan et al. |
| 5,792,204 A | 8/1998 | Snell |
| 5,902,249 A | 5/1999 | Lyster |
| 5,913,685 A | 6/1999 | Hutchins |
| 5,944,669 A | 8/1999 | Kaib |
| 6,047,203 A | 4/2000 | Sackner et al. |
| 6,065,154 A | 5/2000 | Hulings et al. |
| 6,096,063 A * | 8/2000 | Lopin .................. A61N 1/3943 607/8 |
| 6,108,197 A | 8/2000 | Janik |
| 6,148,233 A | 11/2000 | Owen et al. |
| 6,201,992 B1 | 3/2001 | Freeman |
| 6,230,054 B1 | 5/2001 | Powers |
| 6,263,238 B1 | 7/2001 | Brewer et al. |
| 6,287,328 B1 | 9/2001 | Snyder et al. |
| 6,304,780 B1 | 10/2001 | Owen et al. |
| 6,319,011 B1 | 11/2001 | Motti et al. |
| 6,334,070 B1 | 12/2001 | Nova et al. |
| 6,356,785 B1 | 3/2002 | Snyder |
| 6,427,083 B1 | 7/2002 | Owen et al. |
| 6,437,083 B1 | 7/2002 | Owen et al. |
| 6,529,875 B1 | 3/2003 | Nakajima |
| 6,546,285 B1 | 4/2003 | Owen et al. |
| 6,671,545 B2 | 12/2003 | Fincke |
| 6,681,003 B2 | 1/2004 | Linder et al. |
| 6,762,917 B1 | 7/2004 | Verbiest et al. |
| 7,065,401 B2 | 6/2006 | Worden |
| 7,559,902 B2 | 7/2009 | Ting et al. |
| 7,865,238 B2 | 1/2011 | Brink |
| 7,870,761 B2 | 1/2011 | Valentine et al. |
| 7,974,689 B2 | 7/2011 | Volpe et al. |
| 8,135,462 B2 | 3/2012 | Owen et al. |
| 8,140,154 B2 | 3/2012 | Donnelly et al. |
| 8,369,944 B2 | 2/2013 | Macho et al. |
| 8,548,557 B2 | 10/2013 | Garstka et al. |
| 8,615,295 B2 | 12/2013 | Savage et al. |
| 8,644,925 B2 | 2/2014 | Volpe et al. |
| 8,897,860 B2 | 11/2014 | Volpe et al. |
| 8,904,214 B2 | 12/2014 | Volpe et al. |
| 8,965,500 B2 | 2/2015 | Macho et al. |
| 9,008,801 B2 | 4/2015 | Kaib et al. |
| 9,089,685 B2 | 7/2015 | Sullivan et al. |
| 9,131,901 B2 | 9/2015 | Volpe et al. |
| 9,132,267 B2 | 9/2015 | Kaib |
| 9,408,548 B2 | 8/2016 | Volpe et al. |
| 9,454,219 B2 | 9/2016 | Volpe et al. |
| 9,592,403 B2 | 3/2017 | Sullivan |
| 2003/0055460 A1* | 3/2003 | Owen .................. A61N 1/0452 607/5 |
| 2003/0158593 A1 | 8/2003 | Heilman et al. |
| 2004/0068301 A1* | 4/2004 | Waltman .................. A61N 1/39 607/5 |
| 2005/0107833 A1 | 5/2005 | Freeman et al. |
| 2005/0107834 A1 | 5/2005 | Freeman et al. |
| 2008/0312709 A1 | 12/2008 | Volpe et al. |
| 2009/0005827 A1 | 1/2009 | Weintraub et al. |
| 2010/0007413 A1 | 1/2010 | Herleikson |
| 2010/0298899 A1 | 11/2010 | Donnelly et al. |
| 2011/0022105 A9 | 1/2011 | Owen et al. |
| 2011/0106190 A1* | 5/2011 | Foeller .................. A61N 1/3904 607/5 |
| 2011/0245888 A1* | 10/2011 | Badelt .................. A61N 1/3975 607/6 |
| 2011/0288604 A1 | 11/2011 | Kaib et al. |
| 2011/0288605 A1 | 11/2011 | Kaib et al. |
| 2012/0112903 A1 | 5/2012 | Kaib et al. |
| 2012/0144551 A1 | 6/2012 | Guldalian |
| 2012/0150008 A1 | 6/2012 | Kaib et al. |
| 2012/0158075 A1 | 6/2012 | Kaib et al. |
| 2012/0265265 A1 | 10/2012 | Razavi et al. |
| 2012/0283794 A1 | 11/2012 | Kaib et al. |
| 2012/0293323 A1 | 11/2012 | Kaib et al. |
| 2012/0302860 A1 | 11/2012 | Volpe et al. |
| 2012/0310315 A1 | 12/2012 | Savage et al. |
| 2013/0085538 A1 | 4/2013 | Volpe et al. |
| 2013/0231711 A1 | 9/2013 | Kaib |
| 2013/0245388 A1 | 9/2013 | Rafferty et al. |
| 2013/0274565 A1 | 10/2013 | Langer et al. |
| 2013/0317852 A1 | 11/2013 | Worrell et al. |
| 2013/0325078 A1 | 12/2013 | Whiting et al. |
| 2014/0025131 A1 | 1/2014 | Sullivan et al. |
| 2014/0070957 A1 | 3/2014 | Longinotti-Buitoni et al. |
| 2014/0163663 A1 | 6/2014 | Poddar et al. |
| 2014/0324112 A1 | 10/2014 | Macho et al. |
| 2014/0378812 A1 | 12/2014 | Saroka et al. |
| 2015/0039053 A1 | 2/2015 | Kaib et al. |
| 2015/0314132 A1* | 11/2015 | Frustaci .................. A61B 5/742 600/411 |
| 2015/0328472 A1 | 11/2015 | Sullivan et al. |
| 2016/0004831 A1 | 1/2016 | Carlson et al. |
| 2016/0082277 A1 | 3/2016 | Foshee, Jr. et al. |

OTHER PUBLICATIONS

LIFECOR LifeVest System Model WCD 3100 Operator's Manual, 2006, PN 20B0040 Rev FI, Zoll Lifecor Corporation, Pittsburgh, PA.

LifeVest Model 4000 Patient Manual, Zoll, 2009, PN 20B0047 Rev B.

Heartstart MRx and XL AED Algorithm—Application Note, Jul. 2001, Edition 2 Philips Healthcare, USA.

The LifeVest Network/Patient Data Management System, Zoll, 2015, 20C0503 Rev A.

Pagan-Carlo, et al., "Encircling Overlapping Multipulse Shock Waveforms for Transthoracic Defibrillation," JACC Journals, Dec. 1998, vol. 32 Issue 7, p. 2065-2071.

* cited by examiner

*DEFIBRILLATOR OUTPUT STAGE WITH DRIVER CIRCUIT WITH BOOST VOLTAGE*

WEARABLE DEFIBRILLATOR WITH OUTPUT STAGE HAVING DIVERTING RESISTANCE

CROSS REFERENCE TO RELATED PATENT APPLICATIONS

This patent application claims priority from U.S. Provisional Patent Application Ser. No. 62/583,924, filed on Nov. 9, 2017.

BACKGROUND

In humans, the heart beats to sustain life. In normal operation, the heart pumps blood through the various parts of the body. More particularly, the various chambers of the heart contract and expand in a periodic and coordinated fashion, which causes the blood to be pumped regularly. More specifically, the right atrium sends deoxygenated blood into the right ventricle. The right ventricle pumps the blood to the lungs, where it becomes oxygenated, and from where it returns to the left atrium. The left atrium pumps the oxygenated blood to the left ventricle. The left ventricle then expels the blood, forcing it to circulate to the various parts of the body.

The heart chambers pump because of the heart's electrical control system. More particularly, the sinoatrial (SA) node generates an electrical impulse, which generates further electrical signals. These further signals cause the above-described contractions of the various chambers in the heart, in the correct sequence. The electrical pattern created by the SA node is called a sinus rhythm.

Sometimes, however, the electrical control system of the heart malfunctions, which can cause the heart to beat irregularly, or not at all. The cardiac rhythm is then generally called an arrhythmia. Arrhythmias may be caused by electrical activity from locations in the heart other than the SA node. Some types of arrhythmia may result in inadequate blood flow, thus reducing the amount of blood pumped to the various parts of the body. Some arrhythmias may even result in a sudden cardiac arrest (SCA). In a SCA, the heart fails to pump blood effectively, and, if not treated, death can occur. In fact, it is estimated that SCA results in more than 250,000 deaths per year in the United States alone. Further, a SCA may result from a condition other than an arrhythmia.

One type of arrhythmia associated with SCA is known as ventricular fibrillation (VF). VF is a type of malfunction where the ventricles make rapid, uncoordinated movements, instead of the normal contractions. When that happens, the heart does not pump enough blood to deliver enough oxygen to the vital organs. The person's condition will deteriorate rapidly and, if not reversed in time, they will die soon, e.g. within ten minutes. A present or prior VF episode is when a person typically starts becoming characterized as a patient in these contexts.

Ventricular Fibrillation can often be reversed using a life-saving device called a defibrillator. A defibrillator, if applied properly, can administer an electrical shock to the heart. The shock may terminate the VF, thus giving the heart the opportunity to resume pumping blood. If VF is not terminated, the shock may be repeated, often at escalating energies.

A challenge with VF is that the electrical shock must be administered very soon after the onset of VF. There is not much time: the survival rate of patients suffering from VF decreases by about 10% for each minute the administration of a defibrillation shock is delayed. After about 10 minutes, the rate of survival for SCA victims averages less than 2%.

For this reason, there have been efforts to make external defibrillators ubiquitous and portable. Plus, for some people who are considered to be at a higher risk of VF or other heart arrythmias, an external Wearable Cardioverter Defibrillator (WCD) system may be worn, and be ready to operate automatically, until they receive an implantable internal cardioverter defibrillator (ICD).

For all such external defibrillator systems, the goal of portability can be facilitated by making an external defibrillator smaller and lighter.

All subject matter discussed in this Background section of this document is not necessarily prior art, and may not be presumed to be prior art simply because it is presented in this Background section. Plus, any reference to any prior art in this description is not, and should not be taken as, an acknowledgement or any form of suggestion that such prior art forms parts of the common general knowledge in any art in any country. Along these lines, any recognition of problems in the prior art discussed in this Background section or associated with such subject matter should not be treated as prior art, unless expressly stated to be prior art. Rather, the discussion of any subject matter in this Background section should be treated as part of the approach taken towards the particular problem by the inventors. This approach in and of itself may also be inventive.

BRIEF SUMMARY

The present description gives instances of external defibrillators, the use of which may help overcome problems and limitations of the prior art.

In embodiments, an external defibrillator has an electrical circuit with a special output stage for the high-voltage defibrillation pulse. The output stage includes switches that can turn on for delivering the pulse, and off during all other times. The output stage also includes a diverting resistance to divert electrical current that could leak into the patient while a capacitor is being charged. An optional detector may notify if a component is malfunctioning. An advantage can be that an external defibrillator may be created according to embodiments that uses, in its output stage, semiconductor switches instead of relays. As semiconductor switches weigh less and occupy less volume than relays, an external defibrillator according to embodiments may have less weight and volume. Especially in wearable defibrillator applications, less weight means less effort to carry and less volume means easier concealment under clothing.

In embodiments, an external defibrillator has an electrical circuit with a special output stage for the high-voltage defibrillation pulse. The output stage includes switches that can turn on for delivering the pulse, and off for all other times. Driver circuits may receive switch signals from a processor and, in response, output control signals for turning the switches on and off. One or more of the driver circuits receives its switch signal in an input node, and outputs its control signal in a main output node that is opto-isolated from the input node. In embodiments, components result in third-party applied defibrillation pulses not being interfered with, especially in wearable defibrillator applications.

These and other features and advantages of the claimed invention will become more readily apparent in view of the embodiments described and illustrated in this specification, namely in this written specification and the associated drawings.

BRIEF DESCRIPTION OF THE DRAWINGS

FIG. 3 is coupled between the main switch and the H-bridge circuit.

FIG. 3 is coupled between high-voltage switches of the H-bridge circuit.

DETAILED DESCRIPTION

As has been mentioned, the present description is about improved defibrillators. Embodiments are now described in more detail.

Figure 1:
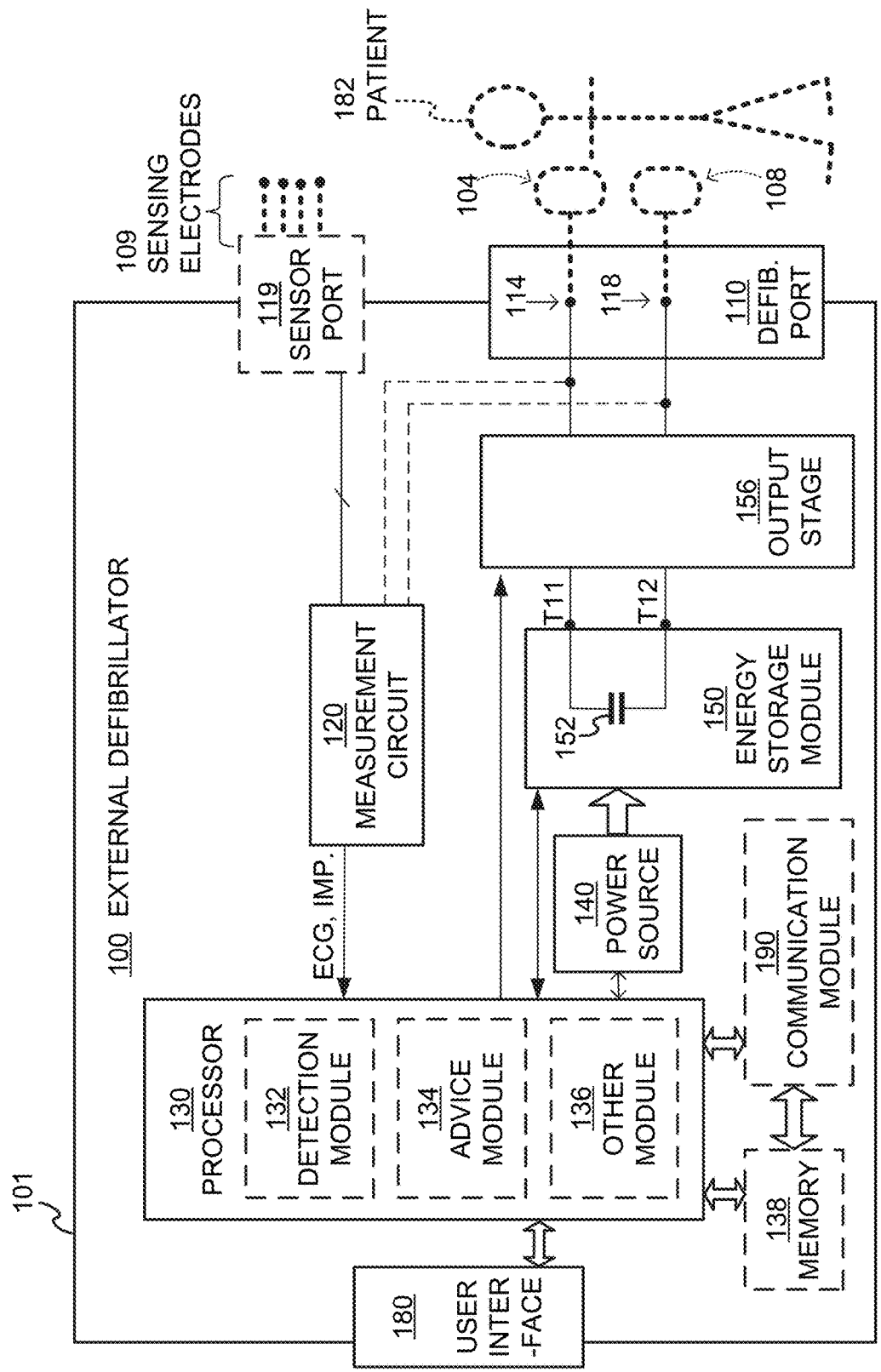
FIG. 1 is a diagram of a sample external defibrillator made according to embodiments.

FIG. 1 is a diagram showing components of an external defibrillator 100, made according to embodiments. The components shown in FIG. 1 can be provided in a housing 101, which may also be referred to as casing 101.

Defibrillator 100 typically includes a defibrillation port 110, which can be a socket in housing 101. Defibrillation port 110 includes electrical nodes 114, 118, which are also known as defibrillation nodes 114, 118.

External defibrillator 100 is intended for a patient 182. Patient 182 may be an SCA victim whom first responders are trying to assist. Or, patient 182 maybe an ambulatory patient who is wearing external defibrillator 100 as part of a Wearable Cardioverter Defibrillator (WCD) system. Indeed, in some embodiments, external defibrillator 100 is part of a Wearable Cardioverter Defibrillator (WCD) system. Such a WCD system may include components described in U.S. patent application Ser. No. 15/927,017, filed on Mar. 20, 2018, published as document US 20180289974, and which is incorporated herein by reference in its entirety.

External defibrillator 100 can be configured to operate with a first defibrillation electrode 104 and a second defibrillation electrode 108. In particular, first defibrillation electrode 104 and second defibrillation electrode 108 can be configured to be coupled to housing 101. For example, leads of defibrillation electrodes 104, 108 can be plugged into defibrillation port 110. This coupling to housing 101 can be configured to cause first defibrillation electrode 104 and second defibrillation electrode 108 to make electrical contact with first defibrillation node 114 and second defibrillation node 118 respectively. It is also possible that defibrillation electrodes 104, 108 are connected continuously to defibrillation port 110, instead.

Moreover, first defibrillation electrode 104 and second defibrillation electrode 108 can be configured to be attached to patient 182. In particular, the pads of electrodes 104, 108 may be applied to the chest of patient 182, for delivering an electrical charge to patient 182 that results in the desired defibrillation shock. It will be understood that the same defibrillator can also deliver a shock of lesser energy for pacing, and so on. Further, in the event that defibrillator 100 is part of a WCD system, electrodes 104, 108 may be applied to the chest continuously.

Defibrillator 100 may further include a user interface 180 for a user, who is not shown. User interface 180 can be made in a number of ways, and include input devices and output devices for its intended user. The user can be a local rescuer at the scene, such as a bystander who might offer assistance, or a trained person. The user can even be patient 182, in the case of a WCD system. Or, the user might be a remotely located trained caregiver in communication with the WCD system.

A number of patient parameters may be collected, such as the patient's ECG. Accordingly, defibrillator 100 may include one or more sensors configured to acquire them. Examples of such sensors or transducers include one or more electrodes to detect ECG data.

Defibrillator 100 may optionally also have a sensor port 119 in housing 101, which is also sometimes known as an ECG port. Sensor port 119 can be adapted for plugging in sensing electrodes 109, which are also known as ECG electrodes and ECG leads. It is also possible that sensing electrodes 109 can be connected continuously to sensor port 119, instead. Sensing electrodes 109 are types of transducers that can help sense an ECG signal, e.g. a 12-lead signal, or a signal from a different number of leads, especially if they make good electrical contact with the body of the patient and in particular with the skin of the patient.

In some embodiments, defibrillator 100 also includes a measurement circuit 120, as one or more of its sensors or transducers. Measurement circuit 120 senses one or more electrical physiological signals of the patient from sensor port 119, if provided. Even if defibrillator 100 lacks sensor port 119, measurement circuit 120 may optionally obtain physiological signals through nodes 114, 118 instead, when defibrillation electrodes 104, 108 are attached to the patient. In these cases, the input reflects an ECG measurement. The patient parameter can be an ECG, which can be sensed as a voltage difference between electrodes 104, 108. For ECG applications, measurement circuit 120 can include 25 kOhm resistors from the defibrillation nodes, then clamps and filters before an ECG amplifier. In addition, the patient parameter can be an impedance, which can be sensed between electrodes 104, 108 and/or between the connections of sensor port 119 considered pairwise. Sensing the impedance can be useful for detecting, among other things, whether these electrodes 104, 108 and/or sensing electrodes 109 are not making good electrical contact with the patient's body. These patient physiological signals may be sensed when available. Measurement circuit 120 can then render or generate information about them as inputs, data, other signals, etc. More strictly speaking, the information rendered by measurement circuit 120 is output from it, but this information can be called an input because it is received as an input by a subsequent device or functionality.

Defibrillator 100 also includes a processor 130. Processor 130 may be implemented in a number of ways. Such ways include, by way of example and not of limitation, digital and/or analog processors such as microprocessors and Digital Signal Processors (DSPs); controllers such as microcontrollers; software running in a machine; programmable circuits such as Field Programmable Gate Arrays (FPGAs), Field-Programmable Analog Arrays (FPAAs), Programmable Logic Devices (PLDs), Application Specific Integrated Circuits (ASICs), any combination of one or more of these, and so on.

Processor 130 may include, or have access to, a non-transitory storage medium, such as memory 138 that is described more fully later in this document. Such a memory can have a non-volatile component for storage of machine-readable and machine-executable instructions. A set of such instructions can also be called a program. The instructions, which may also be referred to as "software," generally provide functionality by performing acts, operations and/or methods as may be disclosed herein or understood by one skilled in the art in view of the disclosed embodiments. In some embodiments, and as a matter of convention used herein, instances of the software may be referred to as a "module" and by other similar terms. Generally, a module includes a set of the instructions so as to offer or fulfill a particular functionality. Embodiments of modules and the functionality delivered are not limited by the embodiments described in this document.

Processor 130 can be considered to have a number of such modules. One such module can be a detection module 132. Detection module 132 can include a Ventricular Fibrillation (VF) detector. The patient's sensed ECG from measurement circuit 120, which can be available as inputs, data that reflect values, or other signals, may be used by the VF detector to determine whether the patient is experiencing VF. Detecting VF is useful, because VF typically results in SCA. Detection module 132 can also include a Ventricular Tachycardia (VT) detector, and so on.

Another such module in processor 130 can be an advice module 134, which generates advice for what to do. The advice can be based on outputs of detection module 132. There can be many types of advice according to embodiments. In some embodiments, the advice is a shock/no shock determination that processor 130 can make, for example via advice module 134. The shock/no shock determination can be made by executing a stored Shock Advisory Algorithm. A Shock Advisory Algorithm can make a shock/no shock determination from one or more ECG signals that are captured according to embodiments, and determine whether or not a shock criterion is met. The determination can be made from a rhythm analysis of the captured ECG signal or otherwise.

In some embodiments, when the determination is to shock, an electrical charge is delivered to patient 182. Delivering the electrical charge is also known as discharging and shocking the patient.

Processor 130 can include additional modules, such as other module 136, for other functions.

In the event that external defibrillator 100 is indeed part of a Wearable Cardioverter Defibrillator (WCD) system, patient 182 is an ambulatory patient, and such a WCD system may further include a support structure that is configured to be worn by the ambulatory patient so as to maintain at least one of defibrillation electrodes 104, 108 on the body of ambulatory patient 182. Defibrillator 100 may also be worn or carried by ambulatory patient 182. In addition, a sensor such as was described above can be configured to sense a parameter of the ambulatory patient, and to render a patient input responsive to the sensed parameter. In such embodiments, processor 130 can be configured to determine from the patient input whether or not a shock criterion is met, and cause, responsive to the shock criterion being met, at least some of the stored electrical charge to be discharged via defibrillation electrode 104, and possibly also 108, through ambulatory patient 182, so as to deliver a shock to ambulatory patient 182.

Defibrillator 100 optionally further includes a memory 138, which can work together with processor 130. Memory 138 may be implemented in a number of ways. Such ways include, by way of example and not of limitation, volatile memories, Nonvolatile Memories (NVM), Read-Only Memories (ROM), Random Access Memories (RAM), magnetic disk storage media, optical storage media, smart cards, flash memory devices, any combination of these, and so on. Memory 138 is thus a non-transitory storage medium. Memory 138, if provided, can include programs for processor 130, which processor 130 may be able to read and execute. More particularly, the programs can include sets of instructions in the form of code, which processor 130 may be able to execute upon reading. Executing is performed by physical manipulations of physical quantities, and may result in functions, operations, processes, acts, actions and/or methods to be performed, and/or the processor to cause other devices or components or blocks to perform such functions, operations, processes, acts, actions and/or methods. The programs can be operational for the inherent needs of processor 130, and can also include protocols and ways that decisions can be made by advice module 134. In addition, memory 138 can store prompts for a user, if this user is a local rescuer. Moreover, memory 138 can store data. This data can include patient data, system data and environmental data. The data can be stored in memory 138 before it is transmitted out of defibrillator 100, or be stored there after it is received by defibrillator 100.

Defibrillator 100 can optionally include a communication module 190, for establishing one or more wired or wireless communication links with other devices of other entities, such as a remote assistance center, Emergency Medical Services (EMS), and so on. The communication links can be used to transfer data and commands. The data may be patient data, event information, therapy attempted, CPR performance, system data, environmental data, and so on. Module 190 may also include such interconnected sub-components as may be deemed necessary by a person skilled in the art, for example an antenna, portions of a processor, supporting electronics, outlet for a telephone or a network cable, etc.

Defibrillator 100 may also include a power source 140. To enable portability of defibrillator 100, power source 140 typically includes a battery. Such a battery is typically implemented as a battery pack, which can be rechargeable or not. Sometimes a combination is used of rechargeable and non-rechargeable battery packs. Other embodiments of power source 140 can include an AC power override, for where AC power will be available, an energy-storing capacitor, and so on. Appropriate components may be included to provide for charging or replacing power source 140. In some embodiments, power source 140 is controlled and/or monitored by processor 130.

Defibrillator 100 may additionally include an energy storage module 150. Module 150 is where some electrical energy can be stored temporarily, when preparing it for discharge to administer a shock. In embodiments, module 150 can be charged from power source 140 to the desired amount of energy, as controlled by processor 130.

In typical implementations, energy storage module 150 includes a charge storage device 152 that has a first terminal T11 and a second terminal T12. Charge storage device 152 may be implemented by a single capacitor, a system of capacitors, an ultracapacitor, and so on. Charge storage device 152 can store charge amounting to enough energy for a defibrillation shock, such as at least 50 Joule (J) of energy, 150 J, 200 J, 360 J, 720 J, and so on. Charge storage device 152 can store lesser amounts of charge, amounting to lesser corresponding energy, for a pacing shock, and so on.

A decision to shock can be made responsive to the shock criterion being met, as per the above-mentioned determination. When the decision is to shock, processor 130 can be configured to cause at least some or all of the electrical charge stored in module 150 to be discharged through patient 182, so as to deliver a shock to patient 182.

For the discharge, defibrillator 100 moreover includes an output stage 156, which can be made according to embodiments described in more detail below. When the decision is to shock, processor 130 can be configured to control output stage 156 to discharge through patient 182 at least some or all of the electrical charge stored in charge storage device 152. Discharging can be to nodes 114, 118, and from there to defibrillation electrodes 104, 108, as mentioned above. Circuit 156 could be thus controlled via processor 130, or via user interface 180, and so on.

A time waveform of the discharge may be controlled by thus controlling output stage 156. The amount of energy of the discharge can be controlled by how much energy storage module has been charged, and also by how long a discharge circuit is controlled to remain open.

Embodiments of output stage 156 are now described in more detail.

In some embodiments, a diverting resistance removes leakage current that might go into the patient. In some of these embodiments, the diverting resistance is coupled across charge storage device 152. Examples are now described.

Figure 2:
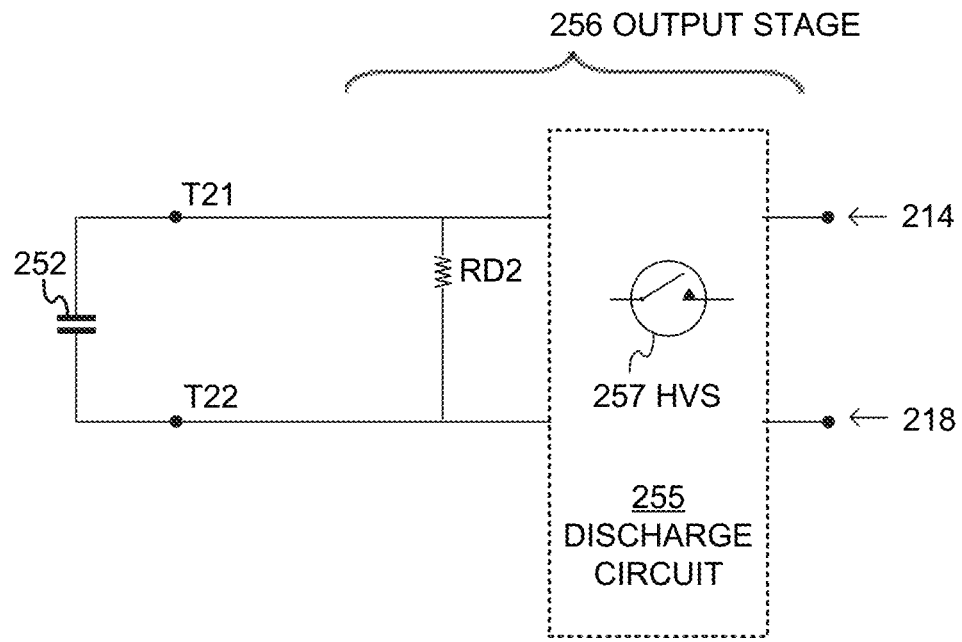
FIG. 2 is a diagram of a sample output stage of a circuit of the defibrillator of FIG. 1, according to embodiments where a diverting resistance is coupled across a charge storage device.

FIG. 2 shows a diagram of a sample output stage 256 of a defibrillator circuit that is made according to embodiments. In the example of FIG. 2, output stage 256 is coupled to a first defibrillation node 214 and a second defibrillation node 218. A charge storage device 252 can be made as mentioned for charge storage device 152, and terminates in a first terminal T21 and a second terminal T22.

Output stage 256 includes a diverting resistance RD2, which is sometimes called a bleed resistance. Diverting resistance RD2 may be implemented in a number of ways according to embodiments, for example by a stand-alone resistor, a series of resistors, a specially created distributed resistance in a semiconductor material, and so on. A good value for a diverting resistance RD2 is 100 kOhm. In the example of FIG. 2, diverting resistance RD2 is coupled across charge storage device 252, by being coupled to terminals T21 and T22.

Output stage 256 also includes a discharge circuit 255. Discharge circuit 255 may include at least one a high-voltage switch (HVS) 257. Often discharge circuit 255 includes more than one HVS, like 2, 4, and so on, as will be seen in examples later in this document.

HVS 257 can be coupled in suitable ways for the discharge. In some embodiments, HVS 257 is coupled between first terminal T21 and first defibrillation node 214. In such embodiments, HVS 257 can be configured to switch on and to switch off so as to respectively couple and uncouple first terminal T11 and first defibrillation node 214.

Figure 3:
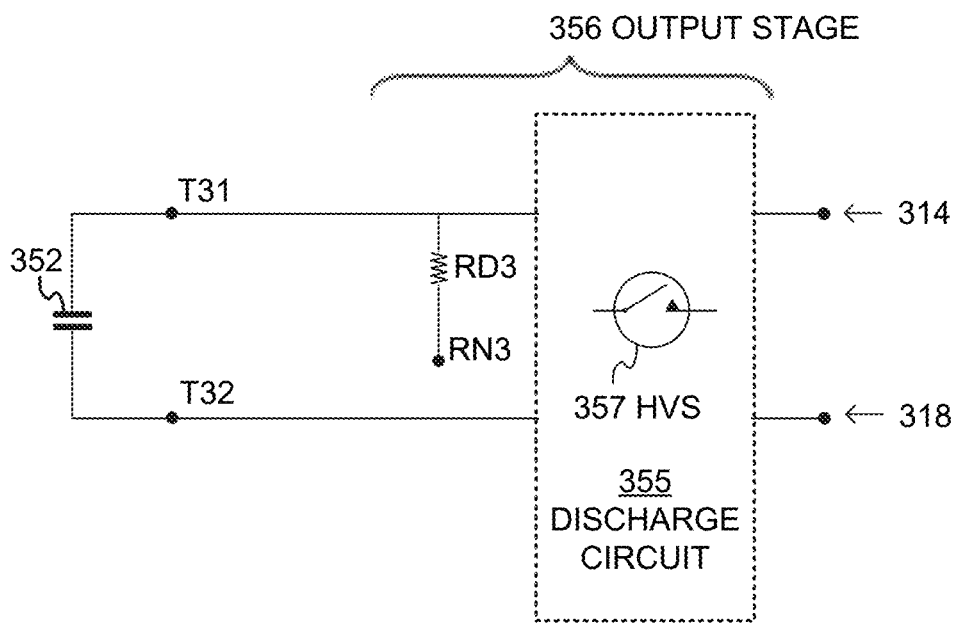
FIG. 3 is a diagram of a sample output stage of a circuit of the defibrillator of FIG. 1, according to embodiments where a diverting resistance is coupled to a reference node.

FIG. 3 shows a diagram of a sample output stage 356 of a defibrillator circuit that is made according to embodiments. In the example of FIG. 3, output stage 356 is coupled to a first defibrillation node 314 and a second defibrillation node 318. A charge storage device 352 can be made as mentioned for charge storage device 152, and terminates in a first terminal T31 and a second terminal T32.

Moreover, a reference node RN3 is maintained at a reference potential. For example, reference node RN3 can be the ground, or maintained at a potential at −20V, +20V, etc. Reference nodes are also sometimes called supply nodes, especially when maintained at a positive potential.

Output stage 356 includes a diverting resistance RD3, which can be made as mentioned for diverting resistance RD2. In the example of FIG. 3, diverting resistance RD3 is coupled between terminal T31 and reference node RN3.

Output stage 356 also includes a discharge circuit 355. Discharge circuit 355 can be made as discharge circuit 255, with HVSs such as HVS 357.

In some embodiments, the defibrillator circuit further includes a detector configured to detect a current leaked through the diverting resistance. In such embodiments, the detector may output a detection signal responsive to the detected leaked current. It will be appreciated that the detection signal can indicate a defect in a high-voltage switch. An example is now described.

Figure 4:
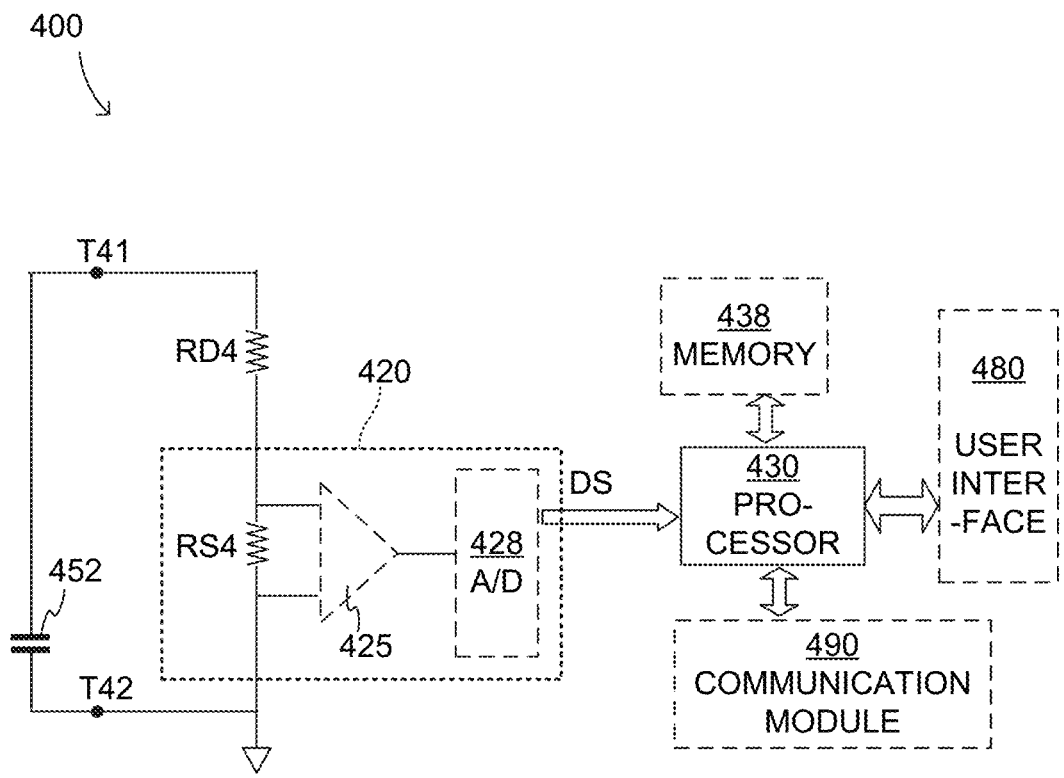
FIG. 4 is a diagram showing sample embodiments of a circuit for a detector of a current leaked through the diverting resistance of FIG. 2 or FIG. 3.

FIG. 4 shows a diagram of a circuit 400, for a detector that could be applied to diverting resistance RD2, RD3. Circuit 400 includes a charge storage device 452, which can be made as mentioned for charge storage device 152 and terminates in first terminal T41 and in second terminal T42. In this example, terminal T42 is coupled to the ground.

Circuit 400 includes a diverting resistor RD4 that can be otherwise coupled as diverting resistance RD2, RD3. In addition, a sense resistor RS4 is series-coupled with diverting resistor RD4. Sense resistor RS4 may have a value of 100 Ohm, i.e. much smaller than diverting resistor RD4. Still, it will be recognized that the total diverting resistance coupled across terminals T41 and T42 is made from both RD4 and RS4. In addition, the total diverting resistance can be considered to use a voltage divider made from both RD4 and RS4.

Sense resistor RS4 has been added so as to create a detector 420. Detector 420 may output a detection signal DS responsive to the detected current that is leaked through diverting resistor RD4 and sense resistor RS4, and especially if the amount of leaked current indicates a failure. In addition to sense resistor RS4, detector 420 includes a detection device 425 coupled to detect a voltage drop across sense resistor RS4. In some embodiments, detection device 425 includes an amplifier, such as a differential amplifier, an operational amplifier, an operational amplifier configured as a differential amplifier, and so on. In some embodiments, detector 420 further includes an analog-to-digital converter 428 coupled to receive an output of detection device 425, for example as shown.

In some embodiments, the defibrillator further includes a processor 430 and a memory 438, which can be made as processor 130 and a memory 138. Processor 430 can be coupled to receive signal DS from detector 420. As such, the voltage across diverting resistor RD4 can be monitored by processor 430 for various instances of the discharge cycle, such as when capacitor 452 is being charged. This can help ensure that the leakage through one of the high-voltage switches is within specification, and therefore a component failure in the output stage can be detected and the user notified that there is a system problem. Notification can happen in a number of ways.

In some embodiments, processor 430 can be configured to record in memory 438 an event responsive to detection signal DS. Such an event may be defect in a high-voltage switch.

In some embodiments, the defibrillator further includes a user interface 480, which can be made as user interface 180. In such embodiments, user interface 480 can be configured to emit a human-perceptible indication responsive to detection signal DS. A human-perceptible indication can be a light, a sound, a tactile output, and so on. The human-perceptible indication may be about a defect in a high-voltage switch.

In some embodiments, the defibrillator further includes communication module 490, which can be made as communication module 190. In such embodiments, communication module 490 can be configured to transmit a message responsive to detection signal DS. The message may be about a defect in a high-voltage switch.

Additional ways of coupling the diverting resistance with the discharge circuit are now described. It will be recognized that a detector, such as detector 420, may be implemented also with those, by making appropriate adjustments.

Figure 5A:
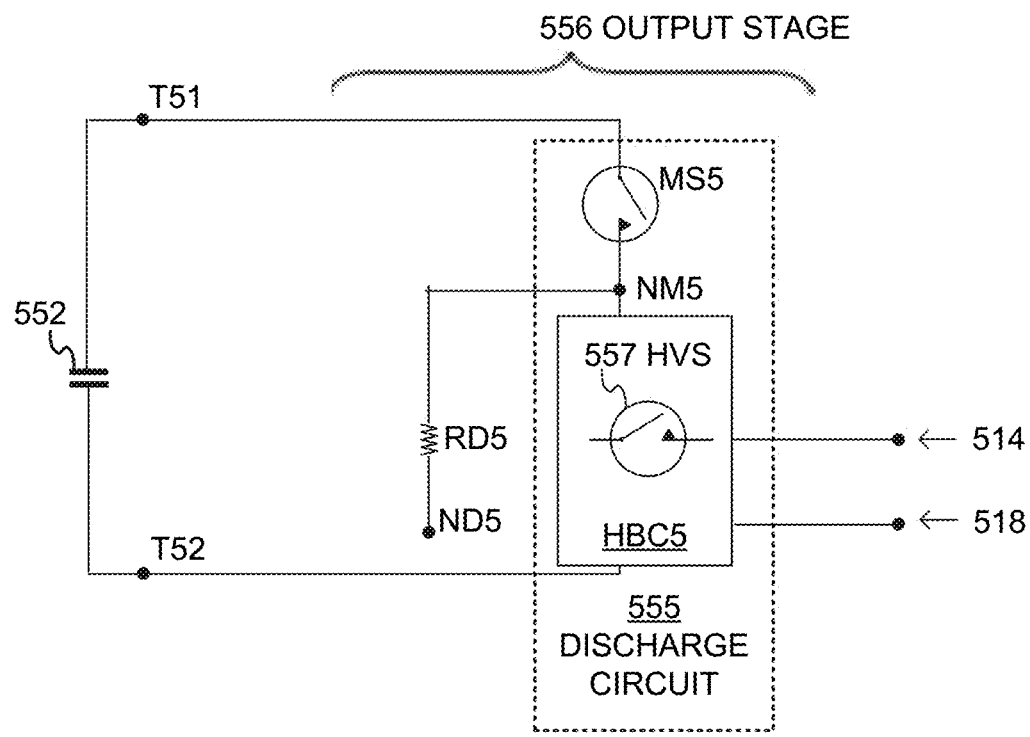
FIG. 5A is a diagram of a sample embodiment where a discharge circuit includes a main switch and an H-bridge circuit, and the diverting resistance of FIG. 2

FIG. 5A shows a diagram of a sample output stage 556 of a defibrillator circuit that is made according to embodiments. In the example of FIG. 5A, output stage 556 is coupled to a first defibrillation node 514 and a second defibrillation node 518. A charge storage device 552 can be made as mentioned for charge storage device 152, and terminates in a first terminal T51 and a second terminal T52.

Figure 5B:
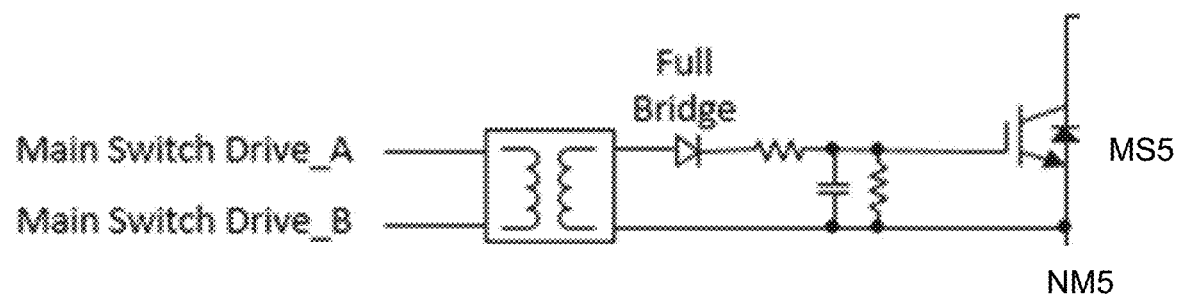
FIG. 5B is a diagram of a sample circuit embodiment for controlling a main switch for the discharge circuit of FIG. 5A.

Output stage 556 includes a discharge circuit 555. Discharge circuit 555 includes a main node NM5, and a main switch MS5 coupled between first terminal T51 and main node NM5. Main switch MS5 can be controlled in a number of ways, for example as shown in FIG. 5B.

Returning to FIG. 5A, output stage 556 also includes an H-bridge circuit HBCS, which may be coupled between main node NM5 and second terminal T2. Examples of H-bridge circuits are described later in this document. H-bridge circuit HBCS may include a high-voltage switch (HVS) 557 as one of its switches. HVS 557 can be coupled as described for HVSs 257, 357, in some instances adjusted for main node NM5, and so on. It will be appreciated that an H-bridge circuit may help with defibrillation pulses that are biphasic, but defibrillation pulses can also be monophasic according to embodiments.

Output stage 556 also includes a diverting node ND5. In some embodiments, diverting node ND5 is second terminal T52, as in FIG. 2. In such embodiments, a diverting resistance RD5 is coupled between second terminal T52 and main node NM5.

In other embodiments, diverting node ND5 is a reference node, such as RN3 of FIG. 3. In such embodiments, a diverting resistance RD5 is coupled between that reference node and main node NM5.

It will be recognized that main switch MS5 provides a second means of protection against the charged energy storage capacitor 552 unintentionally discharging into patient 182 through defibrillation nodes 514, 518. If HVS 557 were to fail and break down, main switch MS5 would prevent current from flowing to the defibrillation electrodes. Conversely, if the main switch MS5 broke down, HVS 557 would prevent current flowing to defibrillation nodes 514, 518. This makes the design fault-tolerant in that regard, and in particular single fault-tolerant. This remains true where HVS 557 is part of an H-bridge, as will be seen below. Main switch MS5 works in conjunction with diverting resistor RD5 to keep the voltage across HVS 557, or at least the upper H-Bridge switches, low while the capacitor is charged.

In some embodiments, the diverting resistance is coupled at an intermediate node of the H-bridge circuit. Examples are now described.

Figure 6:
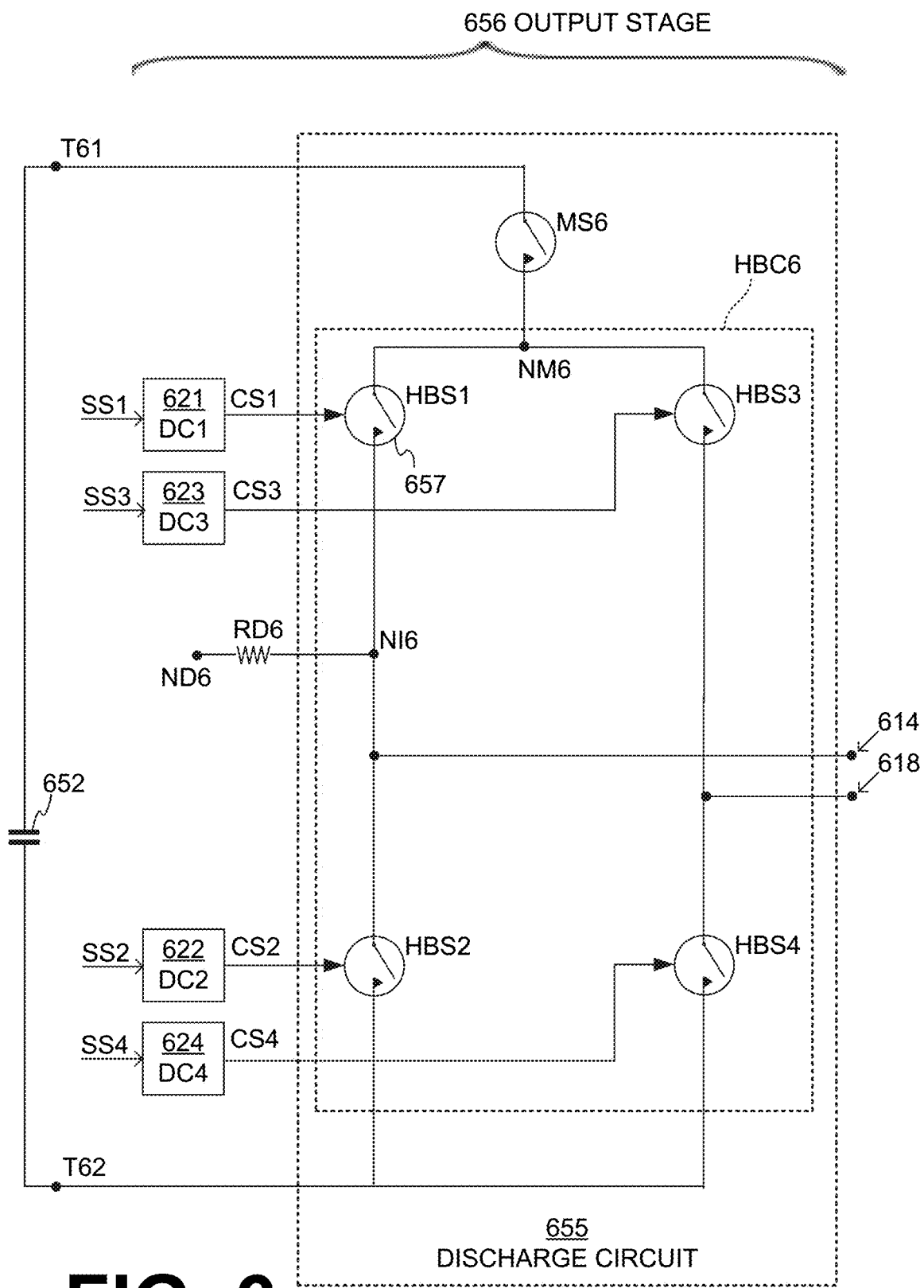
FIG. 6 is a diagram of a sample embodiment where a discharge circuit includes an H-bridge circuit, and the diverting resistance of FIG. 2

FIG. 6 shows a diagram of a sample output stage 656 of a defibrillator circuit that is made according to embodiments. In the example of FIG. 6, output stage 656 is coupled to a first defibrillation node 614 and a second defibrillation node 618. A charge storage device 652 can be made as mentioned for charge storage device 152, and terminates in a first terminal T61 and a second terminal T62.

Output stage 656 includes a discharge circuit 655. Notably, discharge circuit 655 includes an H-bridge circuit HBC6, which is coupled between first terminal T61 and second terminal T62. Optionally, discharge circuit 655 also a main switch MS6 coupled between first terminal T61 and H-bridge circuit HBC6, and main switch MS6 is thus joined with H-bridge circuit HBC6 at a main node NM6.

In the example of FIG. 6, H-bridge circuit HBC6 includes four H-bridge switches HBS1, HBS2, HBS3, HBS4. At least two of these are high-voltage switches. In the example of FIG. 6, H-bridge switch HBS2 is joined with high-voltage switch HBS1 at an intermediate node N16. In some embodiments, as in the example of FIG. 6, intermediate node N16 coincides with first defibrillation node 614. In other embodiments, it may not. For example, in the same branch of high-voltage H-bridge switch HBS1 and before first defibrillation node 614, there could be another H-bridge switch, with the branch therefore having two switches. In such a case, the intermediate node could be between those two switches.

Output stage 656 also includes a diverting node ND6. In some embodiments, diverting node ND6 is second terminal T62, as in FIG. 2. In such embodiments, a diverting resistance RD6 is coupled between second terminal T62 and intermediate node N16. In other embodiments, diverting node ND6 is a reference node, such as RN3 of FIG. 3. In such embodiments, a diverting resistance RD6 is coupled between that reference node and intermediate node N16.

Output stage 656 further includes discharge control circuits DC1 621, DC2 622, DC3 623, DC4 624. These receive respective switch signals SS1, SS2, SS3, SS4 from the processor, which is not shown in FIG. 6. In response to the switch signals, discharge control circuits DC1 621, DC2 622, DC3 623, DC4 624 output control signals CS1, CS2, CS3, CS4 for turning on and off H-bridge switches HBS1, HBS2, HBS3, HBS4.

What was written earlier about detecting a current leaking through the diverting resistance may also be implemented in discharge circuits where the diverting resistance is coupled to a main node, as in FIG. 5A, or to an intermediate node of an H-bridge circuit, as in FIG. 6. An example is now described.

Figure 7:
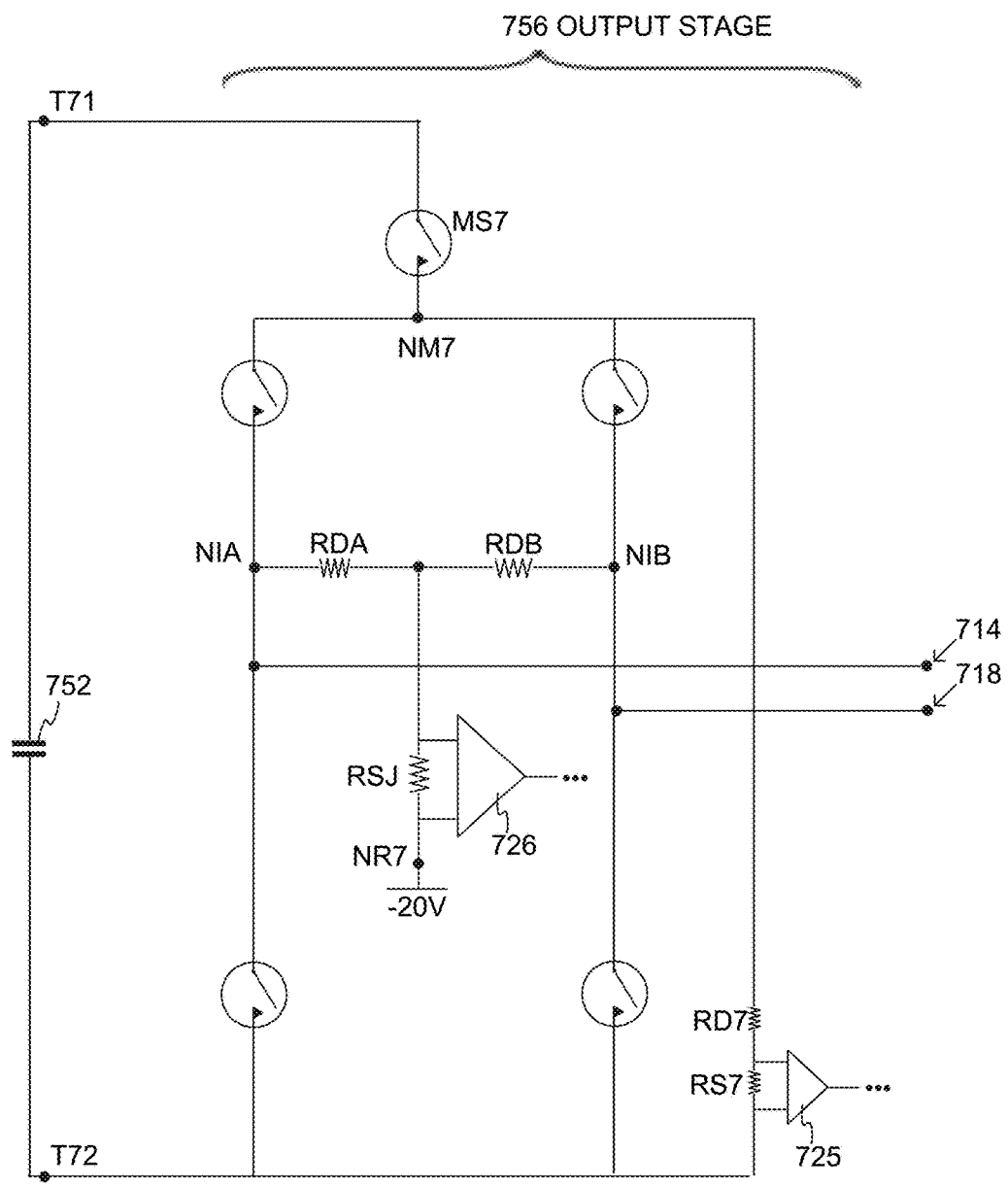
FIG. 7 is a diagram of a sample embodiment like that of FIG. 6, further including leakage current detectors.

FIG. 7 shows a diagram of a sample output stage 756 of a defibrillator circuit that is made according to embodiments. For simplicity, FIG. 7 has similarities with FIG. 6 and, as such, the description of some elements is not repeated. In the example of FIG. 7, output stage 756 is coupled to a first defibrillation node 714 and a second defibrillation node 718. A charge storage device 752 can be made as mentioned for charge storage device 152, and terminates in a first terminal T71 and a second terminal T72.

Output stage 756 includes a main node NM7, and a main switch MS7 coupled between first terminal T71 and main node NM7. Output stage 756 also includes an H-bridge circuit made from four H-bridge switches, similarly with FIG. 6.

A first diverting resistance is made primarily from diverting resistor RD7, coupled between a main node NM7 and second terminal T72. In addition, a first detector is implemented by a sense resistor RS7 coupled in series with diverting resistor RD7. Moreover, an operational amplifier 725 is coupled across the terminals of sense resistor RS7. Additional components are not shown, and they could be as described in FIG. 4.

In FIG. 7, the H-bridge switches further define two intermediate nodes NIA, NIB. Moreover, a reference node NR7 is maintained at a reference potential of −20V.

A second diverting resistance is made from series-coupled diverting resistors RDA and RSJ, coupled between intermediate node NIA and reference node NR7. Plus, a third diverting resistance is made from series-coupled diverting resistors RDB and RSJ, coupled between intermediate node NIB and reference node NR7. These two diverting resistances share resistor RJ, which can thus sense a difference leakage current from perhaps different potentials at intermediate nodes NIA, NIB. As such, RSJ can have a much smaller resistance value to serve as the sense resistor. The voltage drop across resistor RJ can be sensed by operational amplifier 726, as per the above.

It will be appreciated that main switch MS7, in combination with resistance RD7, has the effect of greatly reducing the leakage current through the top H-Bridge switches. This is because the leakage current through a solid state switching device, such as an IGBT, is dependent upon the voltage Vces across the collector and the emitter terminals. Keeping this voltage low, say at approximately 3% of the rated Vces, will keep the leakage current very low. In this design, when the capacitor is being charged, main switch MS7 is allowed to leak up to its maximum rated value, 1 mA for example. At this current, the voltage developed across bleed resistor RD7 and the H-Bridge switches may be limited to 100V, assuming a 100 k bleed resistance as in this example, which would be only 3% of a 3000V rated device. The actual leakage current at 100V is likely not specified in the datasheet for these devices, but nearly all devices will easily be under the 10 uA level required for safety and can be screened accordingly.

In some embodiments, reverse-biased diodes are also used in the H-bridge, to prevent the leakage current from the high voltage switching devices from flowing through the defibrillation electrodes. Especially where the pacing circuit is connected directly to the defibrillation electrodes, reverse biased silicon diodes are used according to embodiments to minimize the leakage current to the patient, and minimize the capacitive loading on the defibrillation electrodes, which in turn can degrade the quality of ECG signal at measurement circuit 120. An example using reverse-biased diodes is now described.

Figure 8:
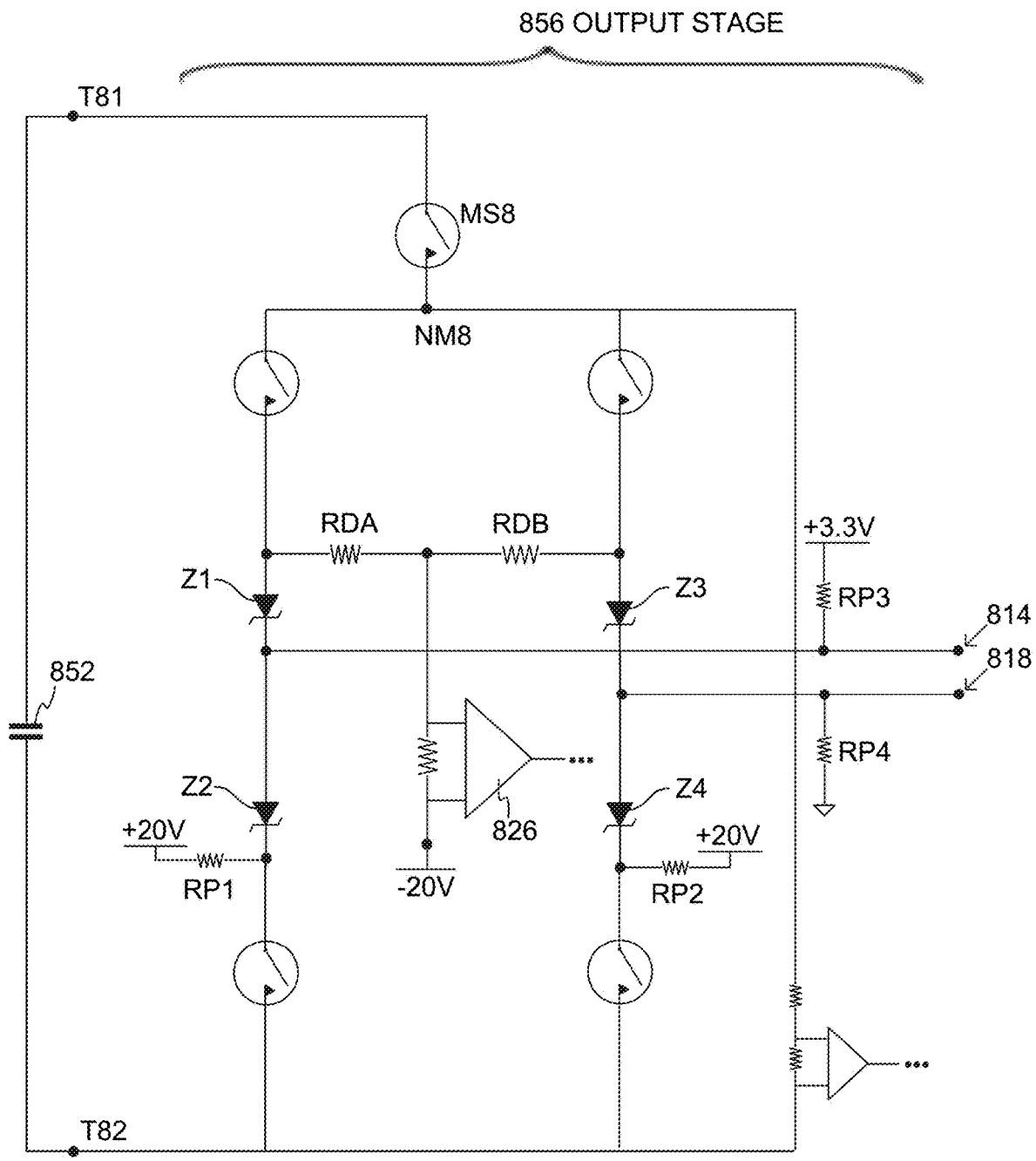
FIG. 8 is a diagram of a sample embodiment like that of FIG. 7, further including reverse-biased diodes.

FIG. 8 shows a diagram of a sample output stage 856 of a defibrillator circuit that is made according to embodiments. For simplicity, FIG. 8 has similarities with FIG. 7 and, as such, the description of some elements is not repeated. In the example of FIG. 8, output stage 856 is coupled to a first defibrillation node 814 and a second defibrillation node 818. A charge storage device 852 can be made as mentioned for charge storage device 152, and terminates in a first terminal T81 and a second terminal T82.

Output stage 856 includes a main node NM8, and an optional main switch MS8 coupled between first terminal T81 and main node NM8. Output stage 856 also includes an H-bridge circuit, similarly with FIG. 7.

Four reverse-biased diodes Z1, Z2, Z3, Z4 are in the four branches of the H-bridge, as shown. Two pull-up resistors RP1 and RP2 reverse-bias diodes Z1, Z2, Z3, Z4 by a reference node of +20V. Diodes Z1, Z2, Z3, Z4 may be zener diodes. In addition, there can be DC leads-off bias of 3.3V and 0V, with a pull-up resistor RP3 of 1.5 MOhm and a pull-down resistor RP4 of 1 MOhm.

Using high voltage diodes in the 1200V range will ensure that, when the diodes are reversed biased by only 1% or 2% of that max reverse bias rating, they will have very low leakage current. In this circuit implementation, the diodes are reverse biased by approximately 20V. The circuit keeps the diodes reversed biased at all times except during therapy pulse delivery.

When the energy storage capacitor is charged, the leakage current through main switch MS8 will cause some voltage drop across the top H-Bridge switches, perhaps up to 100V. Some leakage current will therefore flow through the top H-Bridge switches. Up to 200 uA of current can be allowed to flow through these switches before the voltage drop across the leakage current diverting resistors, RDA and RDB reaches 20V and the diodes start to forward bias. Most, if not all 3000V switching devices will have much less than 200 uA of leakage at 100V. Therefore, the diodes will remain reversed biased and the leakage current to the defibrillation electrodes will be nearly 0.

Maintaining very low leakage current through the output stage also allows for a DC leads-off detection circuit to be implemented using high value resistors that bias the voltage of the electrodes to some middle value, where if one of the electrodes is disconnected from the patient's body, the DC voltages of the electrodes will be pulled to the extremes. In this example, these extremes are 0V and 3.3V, and they can be detected by the ECG Amplifier. If, however, main switch MS8 reverse biased diodes in the output stage were not used, the leakage current through these components could flow through the DC Leads Off Bias resistors, possibly causing a misinterpretation of the true leads-off status.

The capacitance of the reverse biased diodes can also be much lower than that of the high voltage switching devices so the degradation of the ECG signal due to capacitive loading is reduced when compared to circuits with the switching devices connected directly to the defibrillation electrodes.

The leakage current through the top H-Bridge Switches, Q1 and Q2 can be monitored to ensure that they are within specification, by sensing the current through the bias resistors with differential amplifier 826.

Another advantage of the 4 series diodes Z1, Z2, Z3, Z4 is that they can provide blocking protection against an externally applied, third-party defibrillation pulse. Without these diodes, if a high voltage were externally applied between the defibrillation electrodes at nodes 814, 815 in either polarity, the body diodes of the switching devices, IGBTs or BIMOSFETs, would forward bias, which would effectively connect the energy storage capacitor across the defibrillation electrodes. The energy storage capacitor would then absorb a significant portion of the energy being delivered by the external third-party defibrillator, reducing how much of that energy is delivered to the patient. The diodes allow for an external defibrillation pulse of up to twice the breakdown voltage of the diodes to be applied, before any energy will be diverted from the patient into energy storage capacitor 852.

In some embodiments, a discharge circuit includes a high-voltage switch that is controlled by an opto-isolated driver circuit. An example is now described.

Figure 9:
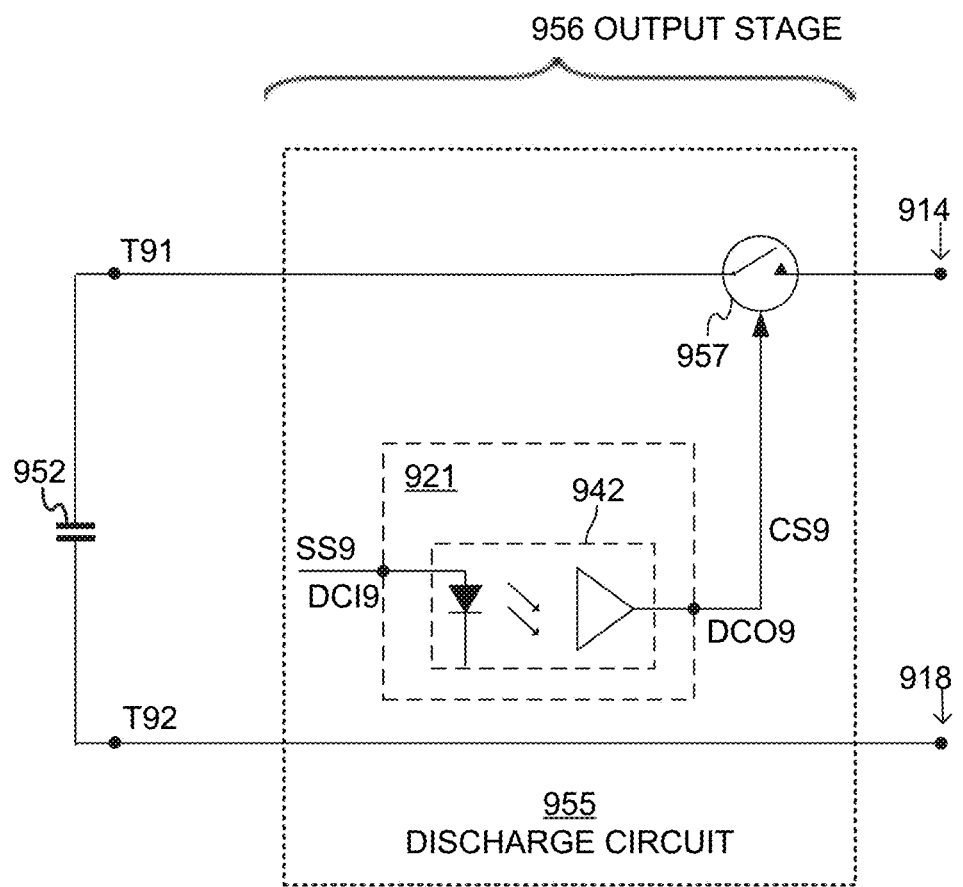
FIG. 9 is a diagram of a sample embodiment where a discharge circuit includes a high-voltage switch that is controlled by an opto-isolated driver circuit.

FIG. 9 shows a diagram of a sample output stage 956 of a defibrillator circuit that is made according to embodiments. In the example of FIG. 9, a discharge circuit 955 coincides with output stage 956. Output stage 956 is coupled to a first defibrillation node 914 and a second defibrillation node 918. A charge storage device 952 can be made as mentioned for charge storage device 152, and terminates in a first terminal T91 and a second terminal T92.

Discharge circuit 955 includes a high-voltage switch 957. Switch 957 can be made and coupled as any of the previously described high-voltage switches, for example HBS1, MS5, and so on. High-voltage switch 957 may be coupled between first terminal T91 and first defibrillation node 914. In some embodiments, the connection may be as simple as shown in FIG. 9. More complex connections are possible in embodiments.

Output stage 956 also includes a driver circuit 921. Driver circuit 921 may have an input node DCI9 that is coupled to receive a switch signal SS9. Driver circuit 921 may also have a main output node DC09 that is configured to output a control signal CS9 responsive to the received switch signal SS9. Main output node DC09 may be opto-isolated from input node DCI9. For example, driver circuit 921 may include an opto-isolated transceiver 942, which can be an off-the-shelf part.

For delivering the defibrillation discharge, therefore, high-voltage switch 957 can be configured to switch on and to switch off responsive to control signal CS9. This switching may couple and uncouple first terminal T91 with first defibrillation node 914.

In some embodiments, high-voltage switch 957 is part of an H-bridge circuit. An example is now described.

Figure 10:
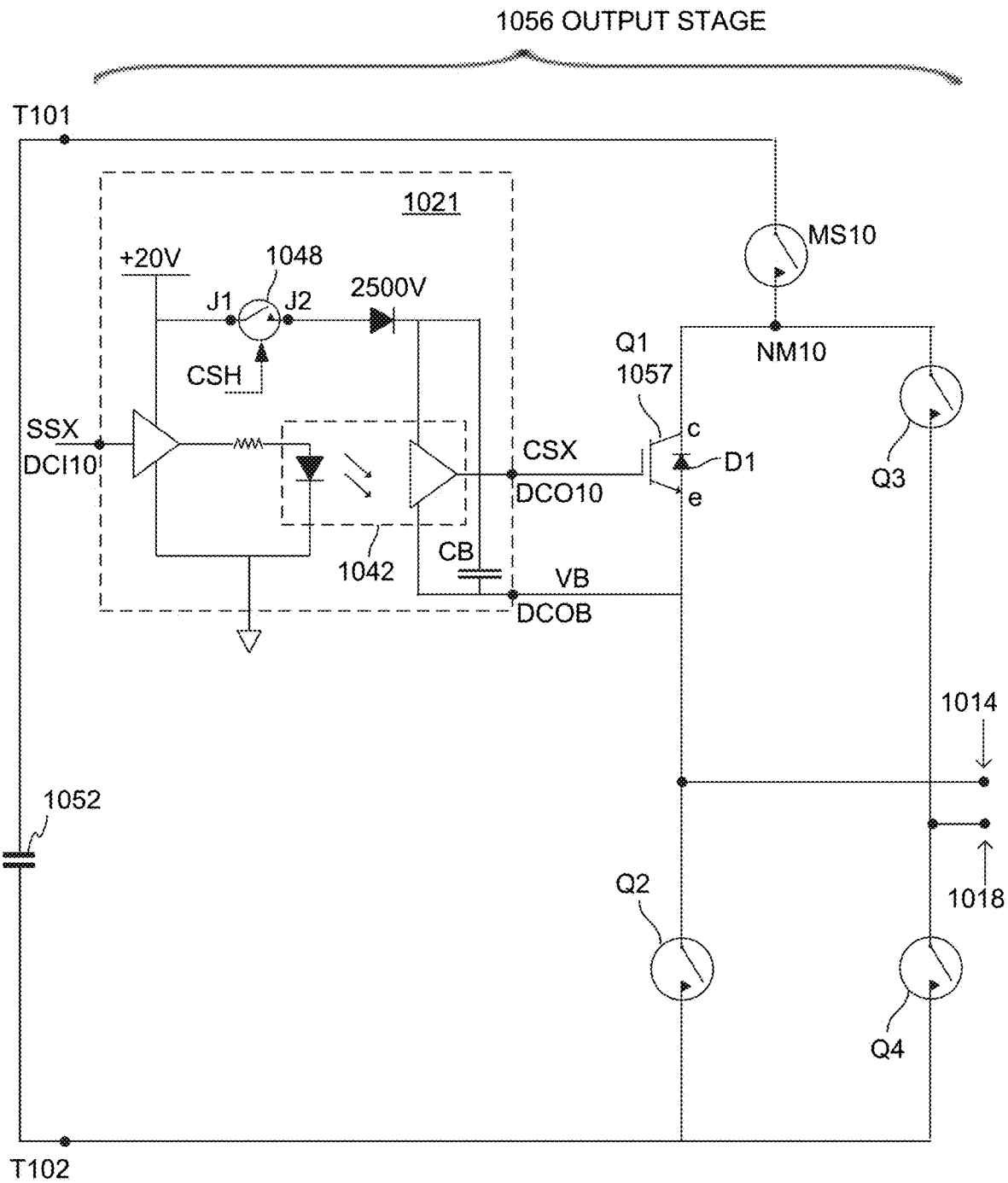
FIG. 10 is a diagram of a sample embodiment where the output stage of FIG. 9 includes an H-bridge circuit.

FIG. 10 shows a diagram of a sample output stage 1056 of a defibrillator circuit that is made according to embodiments. Output stage 1056 is coupled to a first defibrillation node 1014 and a second defibrillation node 1018. A charge storage device 1052 can be made as mentioned for charge storage device 152, and terminates in a first terminal T101 and a second terminal T102. It will be understood that output stage 1056 may also be enhanced with the reverse-biased diodes of FIG. 8.

Output stage 1056 includes a main node NM10, and an optional main switch MS10 coupled between first terminal T101 and main node NM10. Output stage 1056 also includes an H-bridge circuit, with four H-bridge switches Q1 1057, Q2, Q3, Q4 at the four branches of the H-bridge. These are sometime given geography-like designations, for example switch Q1 1057 may be called the NW switch, switch Q3 may be called the NE switch, etc. Switches Q1 and Q3 may also be called the top H-bridge switches.

H-bridge switches Q1 1057, Q2, Q3, Q4 may also have driver circuits, as first indicated in FIG. 6. Driver circuits for H-bridge switches Q2, Q3, Q4 are not shown in FIG. 10, so as not to clutter the drawing.

A driver circuit 1021 controls H-bridge switch Q1 1057. Similarly with what was described with reference to FIG. 9, driver circuit 1021 includes an input node DCI10 coupled to receive a switch signal SSX and a main output node DCO10 configured to output a control signal CSX responsive to the received switch signal SSX. Main output node DCO10 is opto-isolated from input node DCI10 by an opto-isolated transceiver 1042. This may be repeated for additional ones of the driver circuits, and at least for the one of the other top H-bridge switch Q3. Sometimes top, or upper, H-bridge switches Q1, Q3 are driven differently than bottom, or lower top H-bridge switches Q2, Q4.

In the example of FIG. 10, driver circuit 1021 further has an auxiliary output node DCOB distinct from main output node DCO10. Auxiliary output node DCOB can be configured to output a boost voltage VB in coordination with control signal CSX. This driver circuit 1021 may be repeated for additional ones of the driver circuits, and at least for the one of the other top H-bridge switch Q3.

H-bridge switch Q1 1057 is a high-voltage switch. In this example, switch Q1 1057 is a transistor having a base coupled to receive signal CSX, and a first switching terminal and a second switching terminal coupled between first terminal T101 and first defibrillation node T1014. The second switching terminal is coupled to auxiliary output node DCOB to receive boost voltage VB. In this particular case, the first switching terminal is a collector (c), and the second switching terminal is an emitter (e).

In the example of FIG. 10, driver circuit 1021 has a boost capacitor CB for providing output boost voltage VB. Driver circuit 1021 also has a high-voltage (2500V) diode, and a high-voltage control switch 1048 that switches on and off responsive to a control signal CSH.

As such, H-bridge switch Q1 1057, and also optionally H-bridge switch Q3 are ultimately driven by optically isolated gate drive transceiver 1042. The secondary, or output, side of transceiver 1042 that drives the gate of the IGBT or BiMOSFET has advantageously been made able to ride up to a high voltage with the emitter of Q1, while continuing to apply a gate emitter voltage to Q1 to keep it turned on. This is accomplished by galvanic isolation within the opto-coupled gate drive transceiver 1042, and a high-voltage diode (2500V) in series with the power supply. The secondary side is powered by bootstrap capacitor CB that is charged just before turning on Q1, by momentarily turning on the corresponding lower H-Bridge switch Q2 to provide a path to ground.

High-voltage control switch 1048 may provide additional benefits, in the event that the defibrillator output stage needs to withstand an external third-party defibrillation pulse, especially if the reverse-biased diodes are used. For simplicity in FIG. 10, high-voltage control switch 1048 is shown between nodes J1, J2.

Since both electrodes 104, 108 have the same impedance to ground, when an isolated voltage source is externally applied to the electrodes by a third part, the applied voltage may split evenly between electrodes 104, 108, and thus also between defibrillation nodes 1014, 1018. For example, if a third-party 1600V external pulse is applied across the electrodes, with the anterior electrode being positive with respect to posterior electrode, then the posterior electrode will go to −800V and the anterior electrode will go to +800V with respect to the device ground. The anterior electrode may be allowed to go to +800V because of the blocking provided by the series diodes as explained above. However, in order for the posterior electrode to go to −800V, the whole secondary side of isolated gate drive circuit 1021 needs to go to approximately −800V, in which case high-voltage control switch 1048 facilitates disconnecting the secondary's power supply input from the 20V supply. In actual use, switch 1048 only needs to be closed momentarily to charge the bootstrap capacitor CB, just before needing to deliver therapy.

Figure 11:
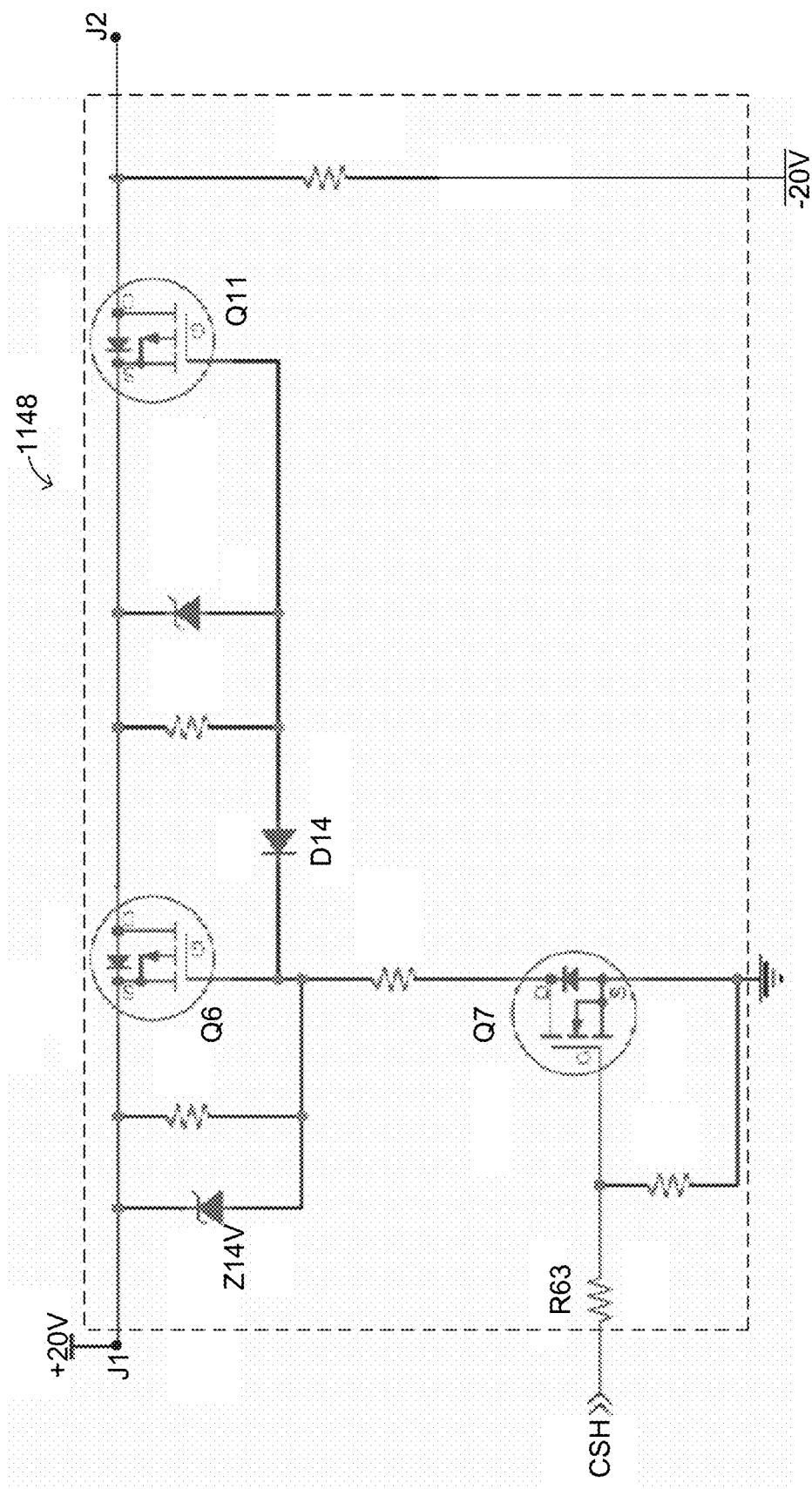
FIG. 11 is a circuit diagram of a sample high-voltage control switch that may be used in a driver circuit of FIG. 10, according to embodiments.

FIG. 11 is a circuit diagram of a sample high-voltage control switch 1148. Switch 1148 may be used in driver circuit 1021 of FIG. 10 in place of switch 1048, between nodes J1 and J2, etc.

Switch 1148 includes two serially-coupled transistors Q6, Q11, in order to withstand up to 800V. In this embodiment, Q6, Q11 are 400V-rated P-channel MOSFETs. MOSFETs can be used as they require smaller low profile packages, and are only available in voltages up to 400V. Diode D14 allows the Q11 gate and source go to −400V, so that the two MOSFETs Q6, Q11 can split the voltage drop evenly between them. To turn the switches on, a microprocessor can apply 3.3V to the gate of Q7 via R63, thus turning Q7 on. This will thus apply 14V across the gate-source of Q6, and approximately 13.3V across the gate-source of Q11, thus turning them both on.

In FIG. 11, a negative 20V supply is also used. This supply is also called N20V, and can be used to pull J2 to −20V when the switch is open and is not connected to P20V. This pulling can help reverse bias the 2500V diodes in the Bootstrap Opto Driver Circuit 1021, which in turn prevents any leakage current that may come through Q6 and Q11 and flow into the patient while Q6 and Q11 are off.

Combining the above embodiments may result in even more advantages. For example, an output stage may result that safely transfers energy stored on the energy storage capacitor to the defibrillation electrodes. The output stage may be using small, reliable components, while meeting the safety requirements of IEC standards for leakage current. Such a circuit topology may have significant advantages for wearable defibrillators, where it is desirable to make the electronics packaging very thin so that it can be concealed on the body under clothing. Relays are fairly big devices and there are very few, if any, that have a low-profile and also a current rating high enough for a defibrillator pulse.

A person skilled in the art will be able to practice the present invention in view of this description, which is to be taken as a whole. Details have been included to provide a thorough understanding. In other instances, well-known aspects have not been described, in order to not obscure unnecessarily this description.

Some technologies or techniques described in this document may be known. Even then, however, it does not necessarily follow that it is known to apply such technologies or techniques as described in this document, or for the purposes described in this document.

This description includes one or more examples, but this fact does not limit how the invention may be practiced. Indeed, examples, instances, versions or embodiments of the invention may be practiced according to what is described, or yet differently, and also in conjunction with other present or future technologies. Other such embodiments include combinations and sub-combinations of features described herein, including for example, embodiments that are equivalent to the following: providing or applying a feature in a different order than in a described embodiment; extracting an individual feature from one embodiment and inserting such feature into another embodiment; removing one or more features from an embodiment; or both removing a feature from an embodiment and adding a feature extracted from another embodiment, while providing the features incorporated in such combinations and sub-combinations.

In general, the present disclosure reflects preferred embodiments of the invention. The attentive reader will note, however, that some aspects of the disclosed embodiments extend beyond the scope of the claims. To the respect that the disclosed embodiments indeed extend beyond the scope of the claims, the disclosed embodiments are to be considered supplementary background information and do not constitute definitions of the claimed invention.

In this document, the phrases "constructed to" and/or "configured to" denote one or more actual states of construction and/or configuration that is fundamentally tied to physical characteristics of the element or feature preceding these phrases and, as such, reach well beyond merely describing an intended use. Any such elements or features can be implemented in a number of ways, as will be apparent to a person skilled in the art after reviewing the present disclosure, beyond any examples shown in this document.

Any and all parent, grandparent, great-grandparent, etc. patent applications, whether mentioned in this document or in an Application Data Sheet ("ADS") of this patent application, are hereby incorporated by reference herein as originally disclosed, including any priority claims made in those applications and any material incorporated by reference, to the extent such subject matter is not inconsistent herewith.

In this description a single reference numeral may be used consistently to denote a single item, aspect, component, or process. Moreover, a further effort may have been made in the drafting of this description to use similar though not identical reference numerals to denote other versions or embodiments of an item, aspect, component or process that are identical or at least similar or related. Where made, such a further effort was not required, but was nevertheless made gratuitously so as to accelerate comprehension by the reader. Even where made in this document, such a further effort might not have been made completely consistently for all of the versions or embodiments that are made possible by this description. Accordingly, the description controls in defining an item, aspect, component or process, rather than its reference numeral. Any similarity in reference numerals may be used to infer a similarity in the text, but not to confuse aspects where the text or other context indicates otherwise.

The claims of this document define certain combinations and subcombinations of elements, features and acts or operations, which are regarded as novel and non-obvious. Additional claims for other such combinations and subcombinations may be presented in this or a related document. These claims are intended to encompass within their scope all changes and modifications that are within the true spirit and scope of the subject matter described herein. The terms used herein, including in the claims, are generally intended as "open" terms. For example, the term "including" should be interpreted as "including but not limited to," the term "having" should be interpreted as "having at least," etc. If a specific number is ascribed to a claim recitation, this number is a minimum but not a maximum unless stated otherwise. For example, where a claim recites "a" component or "an" item, it means that it can have one or more of this component or item.

In construing the claims of this document, the inventor(s) invoke 35 U.S.C. § 112(f) only when the words "means for" or "steps for" are expressly used in the claims. Accordingly, if these words are not used in a claim, then that claim is not intended to be construed by the inventor(s) in accordance with 35 U.S.C. § 112(f).

What is claimed is:

1. A wearable cardioverter defibrillator (WCD) system for an ambulatory patient, comprising:
a first defibrillation electrode and a second defibrillation electrode to contact a body of the ambulatory patient;
a housing having a first defibrillation node and a second defibrillation node, in which the first defibrillation electrode and the second defibrillation electrode are configured to be coupled to the housing so as to make electrical contact with the first defibrillation node and the second defibrillation node;

a charge storage device within the housing and configured to store charge amounting to at least 50 joules of energy, the charge storage device having a first terminal and a second terminal;

a diverting resistance;

a discharge circuit within the housing and including at least two high-voltage transistor switches between the first terminal of the charge storage device and the first defibrillation node, the high-voltage transistor switches configured to switch on and to switch off to respectively couple and uncouple the first terminal and the first defibrillation node, wherein the discharge circuit comprises:

a main node, a main transistor switch coupled with the first terminal of the charge storage device and the main node, and an H-bridge circuit that includes the high-voltage transistor switches, the H-bridge circuit coupled with the main node and the second terminal of the charge storage device, wherein the main transistor switch is between the H-bridge circuit and the charge storage device, wherein the diverting resistance is coupled with the second terminal of the charge storage device and the main node and coupled in parallel with the H-bridge circuit; and wherein the H-bridge circuit comprises a reverse bias Zener diode coupled in series with each of the high-voltage transistor switches, the reverse bias Zener diodes to lower leakage current through the first and second defibrillation electrodes.

2. The WCD system of claim 1, in which
the diverting resistance includes a resistor.

3. The WCD system of claim 1, further comprising:
a detector configured to detect a current leaked through the diverting resistance, and to output a detection signal responsive to the detected leaked current.

4. The WCD system of claim 3, in which
the detector includes:
  a sense resistor coupled in series with the diverting resistance, and
  a detection device coupled to detect a voltage drop across the sense resistor.

5. The WCD system of claim 4, in which
the detection device includes an amplifier.

6. The WCD system of claim 4, in which
the detector further includes an analog-to-digital converter.

7. The WCD system of claim 3, further comprising:
a memory; and
a processor coupled to the detector and configured to record in the memory an event responsive to the detection signal.

8. The WCD system of claim 3, further comprising:
a user interface configured to emit a human-perceptible indication responsive to the detection signal.

9. The WCD system of claim 3, further comprising:
a communication module configured to transmit a message responsive to the detection signal.

10. The WCD system of claim 1, in which
wherein the high-voltage transistor switches are coupled with an intermediate node.

11. The WCD system of claim 10, further comprising:
a detector configured to detect a current leaked through the diverting resistance, and to output a detection signal responsive to the detected leaked current.

12. The WCD system of claim 10, in which
the intermediate node coincides with the first defibrillation node.

13. The WCD system of claim 12, further comprising
a main switch coupled between the first terminal and the H-bridge circuit.

14. The WCD system of claim 12, further comprising:
a detector configured to detect a current leaked through the diverting resistance, and to output a detection signal responsive to the detected leaked current.

15. A wearable cardioverter defibrillator (WCD) system for an ambulatory patient, comprising:
a first defibrillation electrode and a second defibrillation electrode to contact a body of the ambulatory patient;

a housing having a first defibrillation node and a second defibrillation node, in which the first defibrillation electrode and the second defibrillation electrode are configured to be coupled to the housing so as to make electrical contact with the first defibrillation node and the second defibrillation node;

a charge storage device within the housing and configured to store charge amounting to at least 50 joules of energy, the charge storage device having a first terminal and a second terminal;

a reference node to be maintained at a reference potential, wherein the reference potential comprises a positive supply potential or a negative supply potential;

a diverting resistance;

a discharge circuit within the housing and including at least two high-voltage transistor switches between the first terminal of the charge storage device and the first defibrillation node, the high-voltage transistor switches configured to switch on and to switch off to respectively couple and uncouple the first terminal and the first defibrillation node, wherein the discharge circuit comprises:

a main node, a main transistor switch coupled with the first terminal of the charge storage device and the main node, and an H-bridge circuit that includes the high-voltage transistor switches, the H-bridge circuit coupled with the main node and the second terminal of the charge storage device, wherein the main transistor switch is between the H-bridge circuit and the charge storage device, wherein the diverting resistance is coupled with the reference node and the main node and coupled in parallel with the H-bridge circuit; and wherein the H-bridge circuit comprises a reverse bias Zener diode coupled in series with each of the high-voltage transistor switches, the reverse bias Zener diodes to lower leakage current through the first and second defibrillation electrodes.

16. The WCD system of claim 15, in which
the diverting resistance includes a resistor.

17. The WCD system of claim 15, further comprising:
a detector configured to detect a current leaked through the diverting resistance, and to output a detection signal responsive to the detected leaked current.

18. The WCD system of claim 17, in which
the detector includes:
  a sense resistor coupled in series with the diverting resistance, and a detection device coupled to detect a voltage drop across the sense resistor.

19. The WCD system of claim 18, in which the detection device includes an amplifier.

20. The WCD system of claim 18, in which the detector further includes an analog-to-digital converter.

21. The WCD system of claim 17, further comprising:
a memory; and
a processor coupled to the detector and configured to record in the memory an event responsive to the detection signal.

22. The WCD system of claim 17, further comprising:
a user interface configured to emit a human-perceptible indication responsive to the detection signal.

23. The WCD system of claim 17, further comprising:
a communication module configured to transmit a message responsive to the detection signal.

24. The WCD system of claim 15, in which
wherein the high-voltage transistor switches are coupled with an intermediate node.

25. The WCD system of claim 24, further comprising:
a detector configured to detect a current leaked through the diverting resistance, and to output a detection signal responsive to the detected leaked current.

26. The WCD system of claim 24, in which
the intermediate node coincides with the first defibrillation node.

27. The WCD system of claim 26, further comprising:
a main switch coupled between the first terminal and the H-bridge circuit.

28. The WCD system of claim 26, further comprising:
a detector configured to detect a current leaked through the diverting resistance, and to output a detection signal responsive to the detected leaked current.

* * * * *